(12) United States Patent  
Van Mechelen et al.

(10) Patent No.: US 9,304,046 B2
(45) Date of Patent: Apr. 5, 2016

(54) SENSOR SYSTEM AND METHOD FOR CHARACTERIZING A COATED BODY

(71) Applicant: ABB Technology AG, Zurich (CH)

(72) Inventors: Jacobus Lodevicus Martinus Van Mechelen, Regensdorf (CH); Hannes Merbold, Zürich (CH)

(73) Assignee: ABB Technology AG, Zurich (CH)

(*) Notice: Subject to any disclaimer, the term of this patent is extended or adjusted under 35 U.S.C. 154(b) by 0 days.

(21) Appl. No.: 14/607,726

(22) Filed: Jan. 28, 2015

(65) Prior Publication Data

US 2015/0211934 A1 Jul. 30, 2015

(30) Foreign Application Priority Data

Jan. 28, 2014 (EP) ..................................... 14152842

(51) Int. Cl.
| | |
|---|---|
| *G01J 5/02* | (2006.01) |
| *G01J 5/10* | (2006.01) |
| *G01N 21/3563* | (2014.01) |
| *G01J 5/58* | (2006.01) |
| *G01B 11/06* | (2006.01) |

(52) U.S. Cl.
CPC ............... *G01J 5/10* (2013.01); *G01B 11/0625* (2013.01); *G01B 11/0683* (2013.01); *G01J 5/58* (2013.01); *G01N 21/3563* (2013.01)

(58) Field of Classification Search
CPC ........... G01N 21/3586; G01N 21/3581; G02F 2203/13
See application file for complete search history.

(56) References Cited

U.S. PATENT DOCUMENTS

| | | | | |
|---|---|---|---|---|
| 6,057,928 | A * | 5/2000 | Li et al. | 356/445 |
| 8,759,778 | B2 * | 6/2014 | Rahman | 250/341.1 |
| 2005/0098728 | A1 * | 5/2005 | Alfano et al. | 250/341.8 |
| 2006/0105321 | A1 * | 5/2006 | Moy et al. | 435/4 |

(Continued)

FOREIGN PATENT DOCUMENTS

| | | |
|---|---|---|
| EP | 2213977 A1 | 8/2010 |
| JP | 2004028618 A | 1/2004 |
| WO | 2009009785 A1 | 1/2009 |

OTHER PUBLICATIONS

Izutani et al., "Measurements of paint thickness of automobiles by using THz Time-Domain Spectroscopy," 2012, IEEE International Conference on Infrared, Millimeter, and Terahertz Waves, pp. 1-2.*
Kawase et al., "THz imaging techniques for nondestructive inspections," 2010, C. R. Physique, vol. 11, pp. 510-518.*

(Continued)

*Primary Examiner* — Kiho Kim
(74) *Attorney, Agent, or Firm* — Whitmyer IP Group LLC

(57) ABSTRACT

A method of characterizing a coated body by at least one coating parameter based on fitting to a physical model is provided. The coated body includes a substrate coated by a polymeric coating such as a paint film, the polymeric coating having at least one layer. The method is carried out by a sensor system in a non-contact manner, the sensor system including an emitter system for emitting THz radiation, a detector system for detecting THz radiation, and a processing unit operationally coupled to the emitter system and the detector system. The method includes: emitting, by the emitter system, a THz radiation signal towards the coated body such that the THz radiation interacts with the polymeric coating; and detecting, by the detector system, a response signal being the detected THz radiation signal having interacted with the polymeric coating.

17 Claims, 6 Drawing Sheets

(56) References Cited

U.S. PATENT DOCUMENTS

2008/0013070 A1* 1/2008 Kawate .......................... 356/51
2013/0154611 A1* 6/2013 Pate et al. .................. 324/76.19

OTHER PUBLICATIONS

Gao et al., "Measurements of negative refractive index from simulative results and experimental data by a new metamaterial smaple," 2013, Physica A, vol. 392, pp. 6506-6511.*

European Search Report Application No. 14 15 2842 Completed: Mar. 25, 2014; Mailing Date: Apr. 4, 2014 pp. 7.
Yasuda, et al.; "Improvement of Minimum Paint Film Thickness for THz Paint Meters by Multiple-Regression Analysis"; Applied Optics, vol. 46, No. 30, Oct. 20, 2007, Optical Society of America (c). 7518-7526.
Yasui, et al.; "Terahertz Paintmeter for Noncontact Monitoring of Thickness and Drying Progress in Paint Film"; Nov. 10, 2005, vol. 44, No. 32; Applied Optics. 6849-6856.

* cited by examiner

SENSOR SYSTEM AND METHOD FOR CHARACTERIZING A COATED BODY

FIELD OF THE INVENTION

Aspects of the invention relate to a method for characterizing a coated body by one or more coating parameters using THz radiation. The body is coated by a polymeric coating such as a paint film, and the coating parameters include, e.g., the thickness of the polymeric coating and the like. Further aspects of the invention relate to a corresponding sensor system.

BACKGROUND OF THE INVENTION

The application of polymeric coating, and in particular paint, can be useful for augmenting protection and aesthetics of a body, or for preparing the body for further processes such as application of further layer(s). In the following, mainly the case of the polymeric coating being a paint film is discussed, but the discussion also applies to bodies coated by other polymeric coatings.

A paint film is typically applied on a substrate in multiple layers, each layer having a different purpose. If the paint is applied on a metallic substrate such as an automobile component, for example, typical layer sequences are (from bottom to top) e-coat, primer, base coat and clear coat, where e-coat and primer e.g. protect against rust, the base coat is mainly for aesthetics and the clear coat for aesthetics and for further environmental protection.

Although the painting industry is more and more automatized by using paint robots, many paint films still show failures in the uniformity or visual appearance of the paint, or are painted on substrates which contain defects themselves. For these reasons, accurate quality control of paint films is an important part of the paint process. One important aspect of quality control is the measurement of the paint thickness, in order to ensure a uniform thickness within a predetermined tolerance range.

Most state-of-the-art techniques for thickness determination determine just the total thickness of the entire paint film. Further, many of these techniques, such as acoustic and magnetic sensing, work only in contact mode. Furthermore, these techniques are paint unspecific, i.e. unable to account for specific properties of particular paint compositions, which results in large error bars, especially for thick layers and multilayers of different paints.

To overcome some of these limitations, recently methods based on THz radiation have been proposed. These THz based new methods allow non-contact measurements and thereby overcome an important drawback of the prior art. For example, JP 2004028618 A and EP 2213977 A1 describe respective methods for determining the thickness of a paint film using THz radiation. The thickness is obtained by subtraction of peak positions of a time-domain signal. The peak positions, together with a known group index of refraction of the paint, allow calculation of the thickness. However, the robustness of this method leaves room for improvement. Also, the method is only reliable for single layers of known paints with a known index of refraction.

Hence, there is still a need to further improve these measurement techniques, e.g. in order to obtain more accurate parameters, such as individual layer thickness(es) and possibly paint identification, for reliable quality control.

SUMMARY OF THE INVENTION

In view of the above, a method characterizing a coated body and a sensor system are provided.

According to a first aspect, a method of characterizing a coated body by at least one coating parameter based on fitting to a physical model is provided. The coated body comprises a substrate coated by a polymeric coating such as a paint film, the polymeric coating having at least one layer. The method is carried out by a sensor system in a non-contact manner, the sensor system comprising an emitter system for emitting THz radiation, a detector system for detecting THz radiation, and a processing unit operationally coupled to the emitter system and the detector system. The method comprises: emitting, by the emitter system, a THz radiation signal towards the coated body such that the THz radiation interacts with the polymeric coating; detecting, by the detector system, a response signal being the detected THz radiation signal having interacted with the polymeric coating; determining model parameters of the physical model by optimizing the model parameters such that a predicted response signal of the physical model is fitted to the detected response signal, the model parameters being indicative of optical properties of the polymeric coating describing the interaction of the THz radiation signal with the polymeric coating; and determining, from the determined model parameters, the at least one coating parameter.

The model parameters include a parameterization of the index of refraction of the at least one layer. In case of the at least one layer being a plurality of layers, the determined model parameters thus include a parameterization of the respective index of refraction of at least one of the plurality of layers, and preferably a parameterization of the respective index of refraction of each of the plurality of layers. The at least one coating parameter includes a thickness of the polymeric coating.

According to a second aspect, a sensor system for characterizing a coated body, the sensor system is provided. The sensor system comprises an emitter system for emitting THz radiation towards the coated body; a detector system for detecting THz radiation coming from the coated body; a positioning system for positioning the emitter system and the detector system relative to the painted body; and a processing unit operationally coupled to the emitter system and the detector system. The sensor system is configured for characterizing a coated body by the method according to the first aspect.

The sensor assembly and method according to embodiments of the invention allow for obtaining an accurate and meaningful set of coating parameter(s), in particular thickness of the coating or at least one layer thereof, reliably. This is achieved by making use of a large amount of information from the detected THz radiation response of the coated body, by fitting the predicted response of a physical model to the detected THz response signal. Thereby, preferably the entire time trace of the detected THz radiation signal is used for the fitting (e.g. by using an error function that is responsive to any deviation between predicted and measured response). By using the entire time trace, the method is extremely sensitive even with respect to small interactions of the THz radiation with the polymeric coating, e.g. small reflected partial waves, and therefore allows for the determination of individual coating parameter(s) even if the optical contrast between the layers is very small.

Another advantage of embodiments of the invention is that the index of refraction is included in the model parameters which are fitted to the detected response signal. Hence no prior knowledge of the index of refraction is necessary.

Thereby, coating parameters can be obtained reliably even for multilayer structures with a plurality of layers of small optical contrast. Thus, the analysis method is able to obtain the thickness of the polymeric coating or layer(s) thereof, and optionally of other coating parameters, from the detected THz response signal. Preferably, these parameters can be determined for all layers from a single measurement.

An advantage of the THz radiation is that the polymeric coating is typically at least partially transparent to the THz radiation, so that depth information is obtained.

Further advantages, features, aspects and details that can be combined with embodiments described herein are evident from the dependent claims, the description and the drawings.

BRIEF DESCRIPTION OF THE DRAWINGS

The details will be described in the following with reference to the figures, wherein.

DETAILED DESCRIPTION OF THE INVENTION

Figure 1:
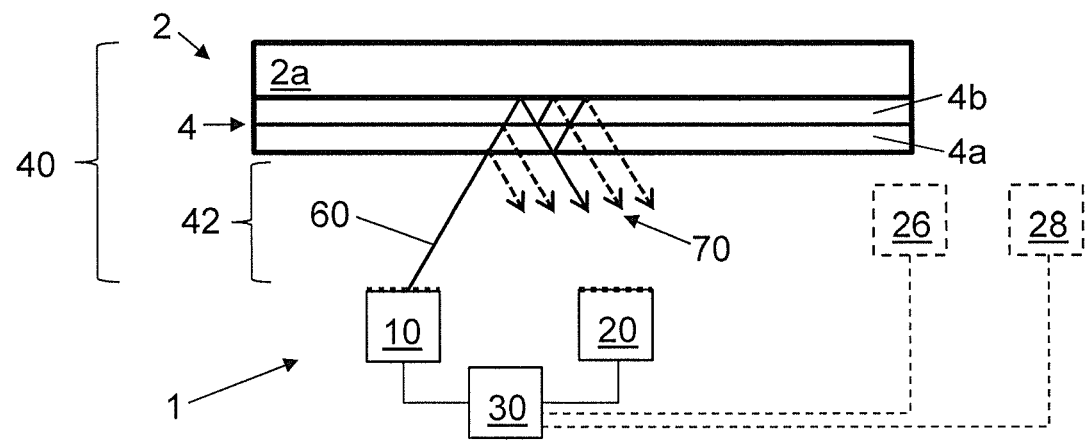
FIG. 1 is a schematic side view of a sensor system according to an embodiment of the invention.

In the following, some more detailed aspects of the invention are described. Unless explicitly stated otherwise, the aspects are independent of each other and can be combined in any manner. For example, any aspect or embodiment described in this document can be combined with any other aspect or embodiment.

First, some general aspects are described. According to an aspect of the invention, the method is carried out by a sensor system in a non-contact manner i.e. without any sensor component requiring direct physical contact with the coated body. This does not exclude a holder holding the coated body, or any further sensor component other than the THz emitter and receiver having contact with the coated body.

According to a further aspect, the coating parameters further include, besides the thickness, at least one of the following (a)-(d), for each or at least for some of the at least one layer of the coating:

(a) a paint type identifier characterizing a type of paint contained in at least one layer of the coating, such as water-borne or solvent-borne paint. Other identifiers may include a characteristic of the absorption spectrum and/or a type of at least one of pigment, additive, and solvent. The paint type identifier is optionally obtained (possibly among others) from a parameter characterizing the frequency-dependence of the index of refraction (or of a quantity related to the index of refraction, such as a transmission or reflection index) of the respective layer.

(b) a specific weight of at least one layer of the coating, wherein the specific weight of the layer is optionally obtained from at least one of the index of refraction and the paint type identifier of the layer.

(c) a defect parameter indicating a defect in at least one layer of the coating.

(d) a total number of layers of the coating.

According to a further aspect, a plurality of the coating parameters, and preferably all of the coating parameters, are obtained coincidentally, using a measurement from the same data source(s), the data source(s) including the THz receiver.

Preferably, a single measured waveform or spectrum is used for determining the plurality of coating parameters. In other words, a plurality and preferably all of the coating parameters are determined from a single response signal. Herein, for example the waveforms of FIGS. 5-8 are understood as a single measured waveform, even if the waveforms are generated from multiple THz pulses. A single measured waveform is understood to be a single curve of continuous time- or frequency-dependence. Normally, a single waveform contains sufficient information for determining the coating parameters of as many layers as is necessary (i.e. as many layers as are present). The method described herein is believed to work for a general number of layers, e.g. for up to 8 layers or even more: In the exceptional case that a single waveform should not contain sufficient information for determining the best-fit response and thereby all coating parameters reliably (e.g. because the mathematical problem is underdetermined), the THz beam can be adapted, e.g. replaced by a longer and thereby more information-rich THz beam. Likewise, a plurality of THz response signals, each from a different emitted THz signal waveforms (reference waveform), may be measured and used simultaneously for optimizing the model parameters. With this approach, it will be possible to distinguish and characterize any given number of layers.

According to a further aspect, the method is based on an analysis of the entire response signal (essentially all data points of the detected THz radiation signal). Thus, any change of the measured response signal (e.g. time trace), at any point, influences the error function associated with a given guess for the simulated response signal, and thereby has an influence on the final result of the predicted response signal. This makes the method extremely sensitive to any information contained in the measured response signal, and allows for the determination of individual layer parameters even though the optical contrast of the layer(s) is very small.

Next, some aspects relating to the coated body are described in more detail. According to one aspect, the polymeric (i.e. polymer-containing, preferably by more than 30 mass % or even more than 50 mass % polymer-containing) coating is a multi-layered coating having at least a first layer and a second layer. The invention also applies to the case of more layers, e.g. three or four layers, etc. According to an aspect, the number of layers is eight or less. The layers are arranged, in thickness direction of the coated body, on top of one another. Hence, the invention is particularly suitable for characterizing substrates on which thin (less than 200 μm thick) coating film is arranged.

According to a further aspect, coating (4) is a paint film, and has at least one of the following layers: (a) an e-coat layer; (b) a primer layer; (c) a base coat layer; and (d) a clear coat layer. Each of these layers, and any other layer of the paint film, is referred to as a paint layer. Thus, even in the absence of other layers, any one of the layers (a) to (d) or any analogous layer is considered as a paint layer.

The coated body may be any coated object. According to a further aspect, coated body is one of an automobile body or other automobile component, a train body or other train component, an aircraft body or other aircraft component, and a wind turbine component.

According to a further aspect, the substrate body comprises at least one of a ferrous metal, a non-ferrous metal, and a fiber composite material.

Next, some aspects relating to the algorithm for finding the predicted response are described in more detail. The algorithm is based on a physical model, i.e. a function outputting a predicted response signal based on model parameters as input variables. In addition, the reference signal and possibly other data such as measured temperature, moisture, and/or other variables are input into the physical model as additional input variables. The physical model is based on physical considerations, e.g. a model describing the interaction of the polymeric layers with the THz radiation in terms of physical laws and in particular of the optical properties of the polymeric layers. The physical model includes a function outputting a predicted response signal based on model parameters (e.g. parameters describing the optical properties of the polymeric layers, in particular a parametrization of their index of refraction) as input variables.

The model parameters may include quantities of interest such as an index of refraction or a parameterization thereof. Further details regarding the model parameters are given below.

According to an aspect, the model parameters of the physical model are determined by optimizing the model parameters such that a predicted response signal of the physical model is fitted to the detected response signal. The algorithm includes the following input data: a reference waveform (in time domain) or reference spectrum (in frequency domain) or some other signal sequence describing the emitted THz radiation signal not having interacted with the coated body, and the detected response having interacted with the coated body. In addition, other parameters characterizing the coated body may be inputted, such as known properties of the paint (e.g. a known parametrization of its index of refraction), known number of layers of paint, known thickness of some layers if available, temperature of the coated body, etc. Likewise, other parameters characterizing the ambient medium may be inputted, such as an ambient moisture and/or a temperature. Any of these parameters can, according to a further aspect, alternatively also be obtained as input parameter which is then determined by the fitting algorithm described herein.

Preferably, an iterative algorithm is used. The iterative algorithm includes the following steps: (a) calculating a simulated (predicted) response based on the physical model using an initial guess for the model parameters; (b) calculating an error function expressing a deviation between the predicted response and the detected response; (c) iterating steps (a) and (b), whereby instead of the initial guess in step (a) the model parameters are updated in order to reduce the error function. These steps (a) and (b) are iterated until the error function satisfies a best-fit criterion. Finally, (d) obtaining the fitted parameters as the final parameters satisfying the best-fit criterion in step (c). Then, at least some of the coating parameters (e.g. thickness) are calculated from the fitted model parameters.

The coating parameters are thus determined by calculating a best-fit response as a function of the model parameters, such that the best-fit response satisfies a predetermined best-fit criterion for an error function expressing a deviation between the predicted response and the detected response. The best-fit criterion may include a minimization criterion for the error function.

The error function may include, e.g., the $L^2$ norm of the difference between the predicted response signal and the measured response signal. Possibly, additional terms may be added to the $L^2$ norm as described below. According to a particular aspect, the error function has a frequency dependent sensitivity. Hence, a particular difference between the frequency-domain predicted response signal and the frequency-domain measured response signal may lead to an error function whose magnitude depends on the frequency at which the difference occurs.

Once the model parameters are determined, at least some of the coating parameters are then calculated from the model parameters.

The iterative best-fit algorithm as described herein ensures a reliable analysis that takes into account the entire information contained in the detected THz radiation signal. Therefore, the result is robust even in case of very weak optical contrast between the layers, because it is based on a large number of data points (entire measured response signal). Further, this approach allows the result to be consistent with a realistic understanding of the underlying physical phenomena present in the coated body.

According to a further aspect, step (a) includes calculating a simulated response signal (94) both in time domain and in frequency domain; step (b) includes calculating the error function as a function of a time-domain error function component and a frequency-domain error function component, e.g. a (possibly weighted) sum or average.

Next, some aspects regarding the model parameters of the physical model are described in more detail. The model parameters are indicative of optical properties of the respective polymeric layers describing the interaction of the THz radiation signal with the respective polymeric layers, and thereby allow calculation of a predicted response signal using the physical model. Also, once the best-fit model parameters are determined, the model parameters allow calculation of the coating parameters.

The model parameters may include, for example, at least one of the index of refraction, indices of transmission and reflection, and a parameterization thereof, preferably such a parameterization that allows for a frequency dependence. In addition, the model parameters may include the number of layers and a thickness of each layer.

The choice of one or more of such model parameters is advantageous because they allow for calculating at least some of the coating parameters relatively straightforwardly. At the same time, these model parameters are directly linked to transmission and/or reflection coefficients via the Fresnel equations (see description of FIG. 4 below), and thereby to the detected response of the THz signal having interacted with the coated body. Thus, a good and robust model of the response of the THz signal having interacted with the coated body is enabled.

Preferably, the physical model and the model parameters enable a parameterization of the index of refraction and/or of the transmission and reflection coefficients such that these quantities have a frequency dependence (e.g. by describing at least one resonance contributing to the index of refraction). In an example, a frequency dependence can be obtained by expressing the transmission and/or reflection coefficients in terms of a frequency-dependent index of refraction of each layer. The frequency-dependent parameterization is preferably based on physical considerations. Preferably, the model parameters allow the index of refraction and/or of the transmission and reflection coefficients to be expressed as complex numbers, i.e. they allow a non-zero imaginary part of these quantities.

In the following, possible model parameters for parameterizing a frequency-dependent index of refraction n(f) of one polymeric layer of the coated body, f being frequency, are given by means of example. Namely, the functional form of n(f) may be expressed using the following parameterization that approximates the expected frequency dependence:

$$n(f)^2 = n_0^2 + \Sigma_k n_k^2 * p_k(f) \quad (1)$$

Herein, k=1 ... N is an index (N being a natural number, e.g. ISM), and $n_0$, $n_k$, are the model parameters, and $p_k(f)$ is a frequency dependent function that represents physical phenomena in the polymeric layer. The parameterization of equations has not only the advantage of approximating the expected form of an index of refraction of a polymeric layer well, but also allows for a physical interpretation of the frequency-dependency being caused by physically relevant modes in the polymeric layer, e.g. absorption modes.

According to a further aspect, the parameterization of the index of refraction includes a frequency-dependent contribution (e.g. the function $p_k(f)$ mentioned above) describing a resonance peak. The frequency-dependent contribution may, for example, be expressable as $$\omega_p^2/(\omega_0^2 - \omega^2 - i\gamma\omega),$$

wherein $\omega = 2\pi f$ is the angular frequency, $\omega_0$ is a peak frequency, $\omega_p$ is a plasma frequency, $\gamma$ is a damping coefficient, and i is the imaginary unit. In a particular example, the peak frequency has a value $\omega_0$ which is within the THz range or at a higher frequency than the THz range. In a further example, there are two frequency-dependent contributions of the above form with different parameters, e.g. one contribution with $\omega_0$ within the THz range and one with $\omega_0$ above or below the THz range, e.g. in the infrared range.

Other specific examples of a functional form of $p_k(f)$ are given below, see the description of FIG. 4. In a variation of this example, any other parameterisation of n(f) or some other parameter indicative of optical properties of the respective layer can be used as well.

Next, some aspects relating to the emitted THz radiation signal and the received (analyzed) THz radiation signal are described in more detail. Herein, THz radiation is defined as electromagnetic radiation of (i.e. including a non-negligible signal component having) a frequency in the range of 0.1-10 THz. The detected signal (e.g. time-domain waveform and/or frequency-domain spectrum of the detected THz radiation) is also referred to as the response signal.

The emitted/received THz radiation signal may be a continuous signal, a THz pulse or partial THz pulse. Herein, a partial pulse or partial wave is defined as partially—in amplitude—reflected or transmitted portions of the emitted pulse/wave: For example, each of the lines corresponding to portions of the response signal 70 in FIG. 3 indicates a partial pulse/wave.

According to a further aspect, the coating parameters are obtained by analyzing a time-domain waveform of the response signal or by analyzing a frequency-domain spectrum of the response signal. According to a preferred aspect, the coating parameters are obtained by analyzing both the time-domain waveform and the frequency-domain spectrum of the response signal.

Next, some aspects relating to further input data are described in more detail. According to a further aspect, the sensor system further comprises an air moisture sensor and/or a temperature sensor operationally coupled to the processing unit, wherein the method further comprises obtaining an ambient air moisture value from the air moisture sensor obtaining a temperature value from the temperature sensor, and inputting the obtained temperature value and/or the ambient air moisture value in the processing unit.

Next, some aspects relating to the geometrical arrangement of the sensor apparatus are described in more detail. According to an aspect, the emitter system and the detector system may be arranged on the same side of the coated body. This is particularly advantageous in the case that the substrate of the coated body is reflective to the THz radiation, e.g. a metal substrate of an automotive body.

Generally, it is preferred (but not required) that the emitter system and the detector system are arranged such that the THz radiation impinges on the coated body in a direction normal to its surface. For example, according to an aspect, the sensor system may comprise a semitransparent THz reflector as beam splitter. The beam splitter may be arranged at an angle with respect to the coated body sheet, such that an optical path from the emitter system and an optical path to the detector system are guided to/from a common optical path that is substantially perpendicular to the coated body. As a result, the emitter system and the detector system are arranged for respectively emitting and detecting light rays having a right angle of incidence with respect to the coated body.

Other arrangements are possible as well. For example, the emitter system and the detector system can be arranged on opposite sides of the coated body for performing a transmission measurement. This is particularly useful if the substrate of the coated body is at least partially transparent to THz radiation (e.g. transmission of at least 0.1% of the beam intensity of the THz radiation).

Next, some aspects relating to the detection of surface roughness are described. These aspects are preferably applicable to the case of a reflection measurement, in which the emitter system and the detector system are arranged on the same side of the coated body. A plurality of response signals are detected by the detector system (20) at least two different positions of the detector system relative to at least one of the emitter system and the surface of the coated body. This may be achieved be moving the detector system, the emitter system and/or the coated body. The motion is such that at least one of the positions of the detector system is away from a direct optical path defined by the emitter system and the surface of the coated body. This direct optical path is defined as the path by which a radiation beam from the emitter system reaches the detector system according to the laws of geometrical optics (Snell's law).

The intensity of the detected signal away from the optical path gives an indication of diffusive reflection caused by a surface roughness of the coated body. Therefore, the analysis of the plurality of detected response signals, in particular their intensities, allows determining the surface roughness. According to a preferred aspect, at least one of the positions is on the direct optical path and at least another one of the positions is away from the direct optical path, and the surface roughness is determined from a comparison of the intensities of the response signals at these positions.

The invention is also directed to systems for performing the methods described herein. According to an aspect, the sensor system comprises an emitter system (10) for emitting THz radiation towards the coated body; a detector system (20) for detecting THz radiation coming from the coated body; a positioning system for positioning the emitter system (10) and the detector system (20) relative to the painted body; and a processing unit (30) operationally coupled to the emitter system (10) and the detector system (20). The sensor system is configured for characterizing a coated body by the method according to any aspect described herein. Herein, the term "configured for" includes that the processing unit is equipped and programmed to this effect. For this purpose, a memory of the processing unit may be equipped with program code for causing a processor of the processing unit to execute the method according to any aspect described herein.

DETAILED DESCRIPTION OF THE FIGURES AND OF EMBODIMENTS

Reference will now be made in detail to the various embodiments, one or more examples of which are illustrated in each figure. Each example is provided by way of explanation and is not meant as a limitation. For example, features illustrated or described as part of one embodiment can be used on or in conjunction with any other embodiment to yield yet a further embodiment. It is intended that the present disclosure includes such modifications and variations.

Within the following description of the drawings, the same reference numbers refer to the same or to similar components. Generally, only the differences with respect to the individual embodiments are described. Unless specified otherwise, the description of a part or aspect in one embodiment applies to a corresponding part or aspect in another embodiment as well.

FIG. 1 is a schematic side view of a sensor system 1 according to an embodiment of the invention. The sensor system 1 has an emitter system 10 for emitting THz radiation, a detector system 20 for detecting THz radiation, and a processing unit 30 operationally coupled to the emitter system 10 and the detector system 20. In addition, FIG. 1 shows an optional additional sensor 26, e.g. an optional humidity measurement device and/or a positioning and/or presence sensor, e.g. for sensing the presence and/or location of a car body. The sensor 26 may also be operationally coupled to the processing unit 30. Herein, "operationally coupled" includes an interface of the processing unit coupled to the respective system, e.g. to the emitter system for triggering emission of THz radiation and to the detector system for receiving measurement data indicative of the response signal.

Further, a coated body 2 is arranged such that the coated body 2 is faced by the emitter system 10 and the detector system 20, with an air gap 42 between the emitter and detector systems 10, 20 on the one side and the coated body 2 on the other side. The coated body 2 has a substrate 2a and a coating 4. In FIG. 1, the coating 4 has two layers 4a and 4b. This number of layers is shown only by means of illustration, and the coating 4 may have any other number of layers, e.g. one layer or three layers. According to a preferred aspect, the described method and system is available for a multi-layered coating having at least two layers.

FIG. 1 also shows the path of a THz radiation signal 60 emitted from the emitter system 10. The THz radiation signal 60 (solid line) traverses the air gap 42 and partly the coated body 2, whereupon it interacts with the coated body. A portion of the THz radiation signal, indicated by the solid line in FIG. 1, is reflected at the surface of substrate 2a and propagates back through the air gap 42 towards the detector system 20. Other portions of the radiation signal 60, indicated by the dashed lines in FIG. 1, are partially reflected at various layer interfaces of the coated body, eventually propagate back towards the THz detector system 20 (as THz response signal 70), and are detected therein. Besides these reflections, also the propagation speed of the various portions of the THz radiation is influenced by and during their interaction with the coated body 2. In this manner, the detected THz signals 70 carry detailed information about the layer(s) of the coated body 2.

Figure 3:
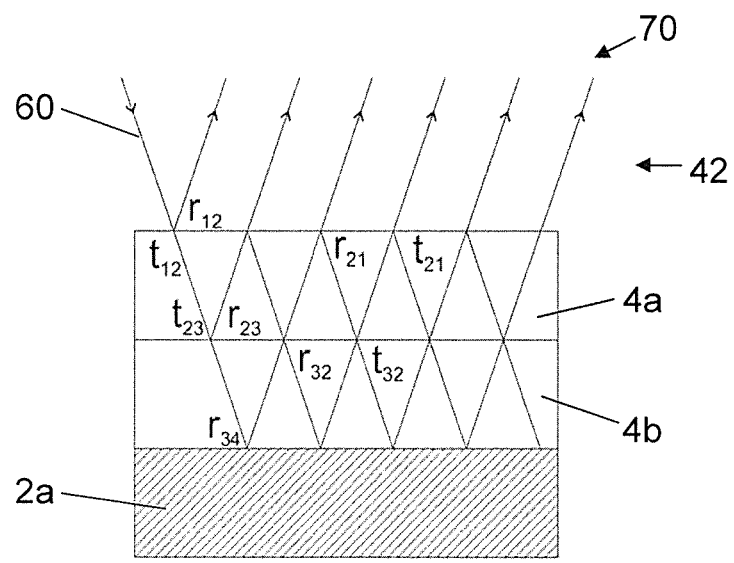
FIG. 3 is a schematic view illustrating the interaction of THz radiation emitted by a sensor system according to an embodiment of the invention with coated body.

FIG. 3 shows the interaction of the THz radiation with the coated body 2 in more detail: At each interface of layers 4a, 4b—either with another layer or with the surrounding medium—a portion of the THz radiation is reflected, and a portion is transmitted. The reflected and transmitted portions are expressed by the complex reflection coefficients $r_{ij}$ and the complex transmission coefficients $t_{ij}$, respectively. Here, the indices ij indicate the boundaries between layers i and j, layer 4a being indicated by i,j=2, layer 4b by i,j=3 and the surrounding medium 42 by i,j=1. The reflection coefficient at the substrate 2 is written as $r_{34}$, i.e. the index j=4 refers to the reflective substrate.

The interaction of the electromagnetic radiation with this multilayer stack (air gaps 42, coated body 2 having substrate 2a and layers 4a, 4b) creates a complex pattern of reflected and transmitted signals. A portion of this THz radiation having interacted with the coated body 2 is detected by the detector system 20. This detected radiation, more precisely the set of data points representing the detected radiation (e.g. represented as a time-domain curve or as a frequency-domain curve as shown in FIGS. 5-12), is also referred to as the THz response signal 70.

The interaction of light with the multilayer structure pictured in FIG. 3 can be described by the Fresnel equations. For a thin film having two layers on a metal substrate in air (refractive index $n_1=1$), the first layer having refractive index $n_2$, thickness $d_2$ and the second layer having refractive index $n_3$, thickness $d_3$, the reflected total electric field $E_r$ can be written as a series of the partial rays:

$$E_r = E_0(r_{12} + t_{12}r_{23}t_{21}e^{-i2\beta} + t_{12}r_{23}r_{21}r_{23}t_{21}e^{i4\beta} + \ldots + t_{12}t_{23}r_{34}t_{32}t_{21}e^{i2\gamma} + t_{12}r_{23}r_{21}r_{23}r_{21}r_{23}t_{21}e^{i6\beta} + \ldots \quad (2)$$

Herein, assuming normal incidence of the radiation, the indices of transmission and reflection $t_{ij}$ and $r_{ij}$ and the phase shifts $\beta$ and $\gamma$ can be expressed as follows:

$$t_{ij} = \frac{2n_i}{n_i + n_j} \quad r_{ij} = \frac{n_i - n_j}{n_i + n_j} \quad (3)$$

$$\beta = \frac{2\pi}{\lambda}d_2n_2 \quad \gamma = \frac{2\pi}{\lambda}(d_2n_2 + d_3n_3)$$

with $\lambda$ the wavelength of the incident light, $n_i$ being the (complex and possibly frequency-dependent) index of refraction, and $d_i$ being the thickness of the respective i-th layer (or air or the substrate) as described above.

The processing section 30 (see FIG. 1) receives the response waveform (THz radiation response) 70, and also receives, or has stored therein, the waveform 60 emitted by the emitter 10. The processing section 30 then performs an analysis of the response waveform (taking into account the original waveform and other information such as detected moisture and/or temperature), and thereby obtains the coating parameters by the method described herein (see e.g. the description of FIG. 4 for additional details).

Figure 2A:
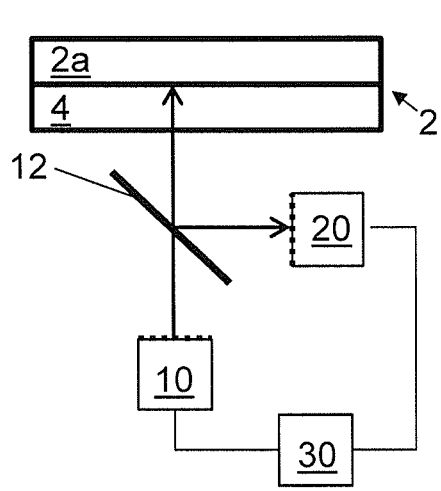
FIGS. 2a and 2b are schematic side views of possible further details and variants of the sensor system of FIG. 1.
Figure 2B:
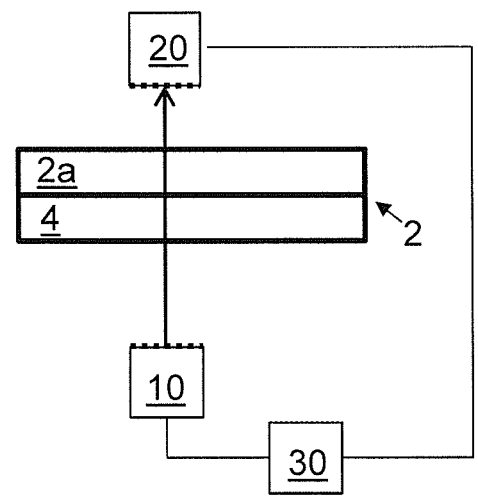

In FIGS. 1 and 3, the radiation is shown to propagate along an angle with respect to the normal direction of the coated body 2. This direction of propagation is mainly for illustration purposes, because it allows for visually separating the incoming and reflected THz radiation. In the actual setup, the main direction of propagation of the THz radiation is preferably normal to the coated body, as shown in FIGS. 2a and 2b below, so that the transmitted and received THz signals are collinear and normal to the surface of the coated body 2. In this manner, a maximum portion of the reflected signals is captured by the detector, and the reflection is minimally influenced by the geometry of the setup. Throughout the description, normal incidence is assumed, although the respective formulae can be generalized to non-normal incidence in a straightforward manner by using the Fresnel equations for non-normal incidence instead of Eq. (2).

FIGS. 2a and 2b are schematic side views of possible further details of possible implementations or variants of the sensor system of FIG. 1. In FIG. 2a, the emitter system 10 and the detector system 20 are arranged with their axes at an angle (here: 90°), and a beam splitter 12 is arranged such as to co-align the axes, so that the transmitted and received THz signals are collinear and normal to the surface of the coated body 2. This arrangement is especially advantageous in the case of the substrate 2a being reflective to THz radiation, e.g. in the case of a metal substrate.

In FIG. 2b, the emitter system 10 and the detector system 20 are arranged on opposite sides of the coated body 2 with their optical axis (direct line between them) being substantially orthogonal to the coated body 2. In this manner, a simple transmission measurement is performed instead of the measurement of the embodiment of FIG. 1. This arrangement is especially advantageous in the case of the substrate 2a being at least partially transmitting THz radiation, e.g. in the case of a resin- or polymer-containing substrate.

In the arrangements of FIGS. 1, 2a and 2b, the detector system 20 may be movable relative to at least one of the emitter system 10 and the surface of the coated body 2, e.g. movable away from a direct optical path. As described above, this allows a measurement of the surface roughness. The relative movement of the detector system 20 may alternatively or additionally be achieved by a movable emitter system and/or a movable coated body.

The resulting waveform of the THz radiation response 70 is influenced by each layer's thickness and optical properties. In particular, the amplitude of each partially reflected beam portion depends on a number of transmission and reflection coefficients, and their time separation (i.e. time difference of the partially reflected beam portion with respect to the emitted beam) depends on the optical thickness of the polymeric coating, as illustrated in FIG. 3 and described above. Hence, the full radiation response 70, together with a reference signal corresponding to the emitted THz signal 60 not having interacted with the coated body, contains sufficient information for the determination of the thickness of the polymeric coatings d2 and d3 of the layers 4a and 4b shown in FIG. 3, and of other coating parameters of the coated body.

In the following, specific aspects of the iterative algorithm for obtaining the thickness of the polymeric coating and other coating parameters are described. The inventors have found that a stable and reliable algorithm is obtained by determining the coating parameters using a physical model. Here, the coating parameters include at least one thickness of the polymeric coating of the coated body, e.g. the thickness of the coating and/or of one or more of its layer(s). For definiteness, the method is illustrated for the case of a substrate 2a on which a polymeric coating consisting of two layers 4a, 4b is arranged (see FIG. 1), and for the following coating parameters to be determined: thicknesses d2, d3 of each of the layers (the thicknesses are collectively labeled as d); and other coating parameters that can be expressed in terms of the frequency-dependent index of refraction n(f) of each layer. The discussion herein can be adapted to the case of determining a thickness of a single layer of the polymeric coating or to the thicknesses of each of more than two layers.

Figure 4:
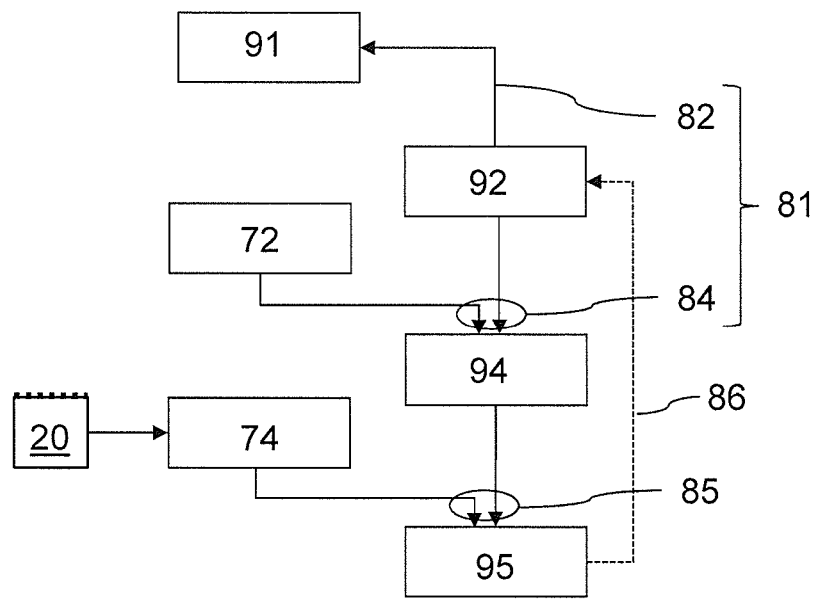
FIG. 4 is a block diagram illustrating a method of characterizing a coated body according to an embodiment of the invention.

This algorithm is illustrated in the block diagram of FIG. 4 in more detail. This algorithm is based on a physical (optical) model 81. The physical model 81 includes a waveform-prediction map 84 that maps the model parameters 92 as input to a predicted waveform 94 as output. Further, the model 81 includes a coating-parameter map 82 that maps the model parameters 92 as input to the coating parameters 91 as output. Herein, the model parameters 92 are, for example, a parameterization of the index of refraction n(f) and the thickness d for each layer; and the predicted waveform 94 is, for example, a predicted form of the response signal 70 (shown as red lines in FIGS. 5-8).

In the following, an example of the waveform-prediction map 84 is described in more detail. As stated above, the waveform-prediction map 84 takes the model parameters 92 as input and outputs a predicted waveform 94. Here, the model parameters are the thickness d for each layer (i.e. in the example thicknesses d2, d3), and a parameterization of the frequency-dependent index of refraction n(f) for each layer.

In the following, preferred aspects of the parameterization of the index of refraction n(f) are described that can be used independently of the given embodiment. The parameterization of the index of refraction is such that the index of refraction has a dependence on frequency, wherein the index of refraction preferably has the form of Eq. (1) above. Preferably, the index of refraction includes a frequency-dependent contribution describing a resonance, and the frequency-dependent contribution is particularly preferably expressable as a function $p_k(f)$ proportional to $$\omega_{p,1}^2/(\omega_0^2=\omega^2-i\gamma_1\omega),$$

wherein $\omega$ is the frequency, $\omega_0$ is an oscillator frequency, $\omega_{p,1}$ is a plasma frequency, $\gamma_1$ is a damping coefficient, and i is the imaginary unit. Alternatively or additionally, a frequency-dependent contribution may be expressable as a function $p_k(f)$ proportional to $$\omega_{p,1}^2/(-\omega^2-i\gamma_1\omega),$$

i.e. as a free oscillator having a peak at zero frequency.

Optionally there are other frequency-dependent contributions/summands, e.g. contributions from other oscillators.

For example, a possible parameterization of the (squared) index of refraction is $$n(\omega)^2 = \epsilon(\omega) + \epsilon_\infty + \sum_{i=1}^{n} \frac{\omega_{p,i}^2}{\omega_{0,1}^2 - \omega^2 - i\gamma_i\omega} \tag{4}$$

where $\epsilon_\infty$ the dielectric constant at high frequencies, and $\omega_0$ the oscillator frequency. A paint layer, as far as its interaction with THz radiation is concerned, can be expressed, for example, by one or two oscillators: One free oscillator (for which $\omega_0=0$); and optionally another oscillator being associated with an absorption band (for which $\omega_0$ has some finite value).

The parameterization as described above is used for each of the layers. Hence, the model parameters in this case are the adjustable parameters in Eq. (4) and the thickness d, for each of the layers. Thus, for example, in the case of layers each being modelled by just one oscillator representing the free (electron) oscillations of the layer (i.e. with $\omega_0=0$), the model parameters for each layer are d, $\in_\infty$, $\omega_{p,1}$ and $\gamma_1$, and the index of refraction is obtained via Eq. (4) with counter n=1 and $\omega_{0,1}^2=0$.

From the thickness d and such a parameterization of the index of refraction n(f), the transmission and/or reflection coefficients can be obtained via Fresnel equations. In the example of the coated body 2 shown in FIG. 3, the reflection and transmission coefficients $r_{ij}$, $t_{ij}$ at the interfaces of the layers 4a, 4b are, for example, given in Eq. (3) above.

The waveform-prediction map 84 further includes a set of optics equations for calculating a predicted response (predicted waveform for the response signal 70) 94. These optics equations may, for example, be expressed by Eq. (2) above. The optics equations have the following input parameters: (i) the waveform $E_0$ of the emitted THz radiation signal 72 (i.e. waveform of emitted radiation 60 of FIGS. 1 and 3), and (ii) the reflection and transmission coefficients ($r_{ij}$, $t_{ij}$) and the phase shifts $\beta$, $\gamma$ from Eq. (3). Other input parameters may be included as well.

The algorithm further includes an error function 85 that expresses a deviation 95 between the predicted response 94 on the one hand and the detected response 74 (waveform of the detected radiation 70 of FIGS. 1, 3) on the other hand. This error function 85 may, for example, be the $L^2$ norm or some other norm as described herein.

Possibly, according to a general aspect of the error function independently of this embodiment, the error function may, include a "penalty term" that penalizes a physically implausible predicted response; and/or a frequency-dependent term that gives additional weight to deviations in a particularly sensitive frequency range. Such a sensitive frequency range may include the frequency range between 0.1 THz and 1 THz at least partially. Such a term may, for example, be added to other contributions such as the $L^2$ norm.

According to a particular aspect, the error function has a frequency dependent sensitivity. Hence, a particular difference between the frequency-domain predicted response signal and the frequency-domain measured response signal may lead to an error function whose magnitude depends on the frequency at which the difference occurs.

Next, the coating-parameter map 82 is described in more detail. As stated above, the coating-parameter map 82 calculates, from the model parameters 92, the coating parameters 91 as output. In the example described above, some coating parameters of the coated body may be obtained from the above parameterization of n(f) as follows:

(a) A paint type identifier characterizing a type of paint may be determined from the parameters parametrizing n($\omega$), e.g. the parameters on the right side of Eq. (4). These values are then matched to a table in which the values or ranges of these parameters for each paint type are defined, and the paint type is determined based on the matching. Alternatively, only a set of discrete parameters parametrizing n($\omega$) may be used as input parameters of the fitting algorithm, each set of parameters corresponding to a known paint type. The set minimizing the error function is then used, and the paint type is determined as the paint type corresponding to the chosen set.

(b) A specific weight of at least one layer of the coating may be directly derived from the paint type identifier of the layer, or may be obtained in a manner analogous to the method discussed in (a) above. Alternatively, for some paints the specific weight may be expressed as a function or functional of the index of refraction, e.g. its value at a particular frequency (such as $\omega=0$) or its integral or L2 norm over a frequency range. The function or functional may also depend on the paint type described above.

(c) a defect parameter indicating a defect in at least one layer of the coating. This defect parameter may be obtained from an abrupt local change in n with respect to its value in neighbouring regions of the coating.

In addition or alternatively, the defect parameter may also be obtained by detecting the presence of an additional layer (e.g. air layer) within the coating at a particular region. According to this aspect, the number of layers is used as a fitting parameter, and a region in which the additional layer is obtained is marked as having a defect.

The thickness d was already used as a fit parameter and is identically used as coating parameter. Likewise, the number of layers N may be used as a (discrete) fitting parameter which is then identically used as a coating parameter.

Next, the iterative algorithm itself, as illustrated in FIG. 4, is described in more detail. In a first step, initial fit parameters 92 are generated, e.g. as random numbers or plausible initial values. In this example, as stated above, the fit parameters are given by the respective thickness and parameters characterizing the respective index of refraction of each layer.

Then, the initial fit parameters 92 are input, together with the reference waveform 72, into the waveform-prediction map 84; and the waveform-prediction map 84 calculates the predicted (simulated) response 94 using this input. Namely, the indices of reflection and transmission and phase shifts are calculated via the Fresnel equations, Eq. (3), and the predicted response 94 is calculated based on these coefficients using the optics equations, Eq. (2), as described above.

Then, the deviation 95 between the predicted response 94 and the measured response 74 is calculated using the error function 85. Then the model parameters 92 are varied depending on the coefficients and error function 85 of previous steps. This variation is performed using a strategy that eventually approaches a minimum deviation. For example, a minimization algorithm based on the Levenberg-Marquardt technique can be used. Then, the algorithm is repeated (arrow 86), now using the varied model parameters 92 instead of the initial parameters.

In this manner, the model parameters (fit parameters) 92 are varied repeatedly in the loop represented by the arrow 86, until the deviation 95 satisfies a best-fit criterion (e.g. until the deviation is sufficiently minimized or until some other cut-off criterion is met).

Then, the final fit parameters 92 of the last step are used for calculating the coating parameters 91 (e.g. thicknesses $d_2$, $d_3$) via the coating-parameter map 82 as described above.

In this manner, the coating parameters 91 are determined by calculating a best-fit response 94 that sufficiently minimizes the deviation 95, i.e. such that the predicted response 94 of the physical model fits to the detected response 74. Since the algorithm takes into account the full waveform of the detected response 74 via the error function 85, and not just individual land-mark features, the result is stable and reliable by the fact that one accounts for each individual frequency component in the appropriate way, given by the physical model.

In alternative embodiments, the frequency-dependent index of refraction n(f) may alternatively also be replaced by another equivalent parameterization, e.g. the conductivity which is proportional to the index of refraction squared multiplied by frequency. Alternatively, also some other parameterization of the optically relevant properties of each layer can be used as fit parameters. For example, in a variation, the coating parameters 91 can be used directly as fit parameters. In another variation, the iterative method can be adapted to more than two layers. To this purpose, Eq (2-3) is to be generalised to more than 2 layers, which is straightforward textbook knowledge. In another variation, additional input parameters may be used (e.g. the index of refraction of the surrounding medium, e.g. air, 42, 44).

In another variation, some parameters described as fitting parameters may be determined using additional sensors or input means. Thus, for example the thickness d2 of the first coating layer 4a may be manually input, and the iterative method described herein may be used only for obtaining the thickness d3 of an additionally applied layer 4b.

Next, some experimental results are discussed with reference to FIGS. 5-8.

Figure 5:
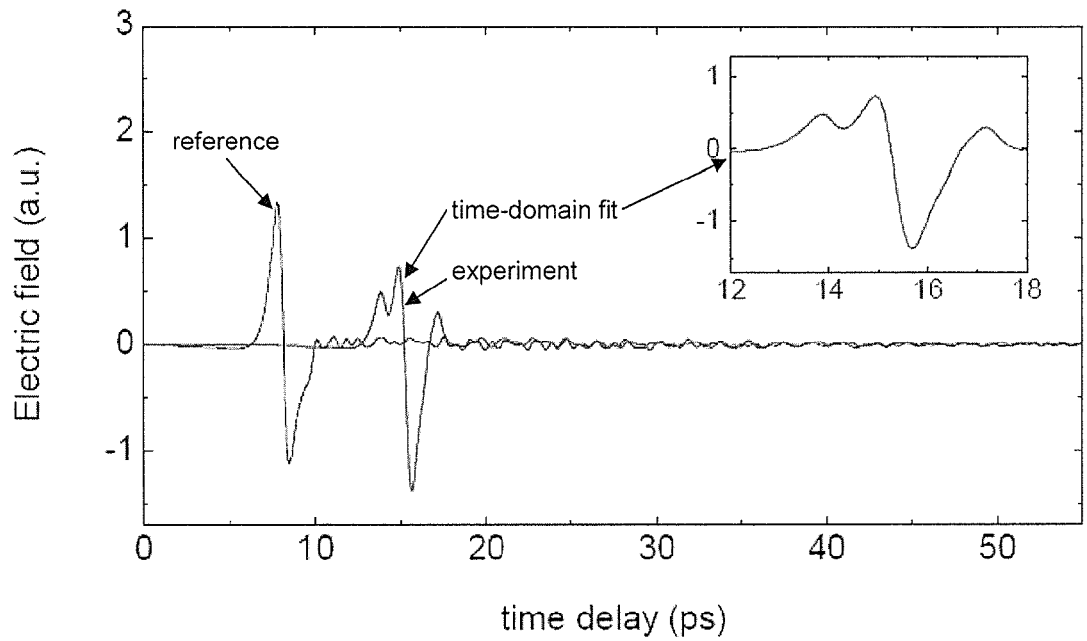
FIG. 5 is a diagram representing the response signal and related quantities measured by a system as shown in FIG. 1 in time domain.

FIG. 5 shows the as-measured time-domain waveform (electric field Er(t)) of a THz radiation signal 70 reflected, in a setup as shown in FIG. 1, by the coated body 2 and measured by the detector 20. The coated body 2 consists of a multilayer paint coat 4 on top of a steel substrate 2a. Different from FIG. 1, the multilayer paint coat is composed of three paint layers: a clear coat, a blue solvent-borne base coat and a white primer.

FIG. 5 shows the electric field Er(t) reflected from the coated body as a function of delay time t (curve: experiment). In addition, FIG. 5 also shows the reference field (curve: reference). The reference field has been obtained by an analogous measurement from an uncoated steel plate used as reference (reference curve), so that the measured signal was not distorted but kept its original waveform.

Figure 6:
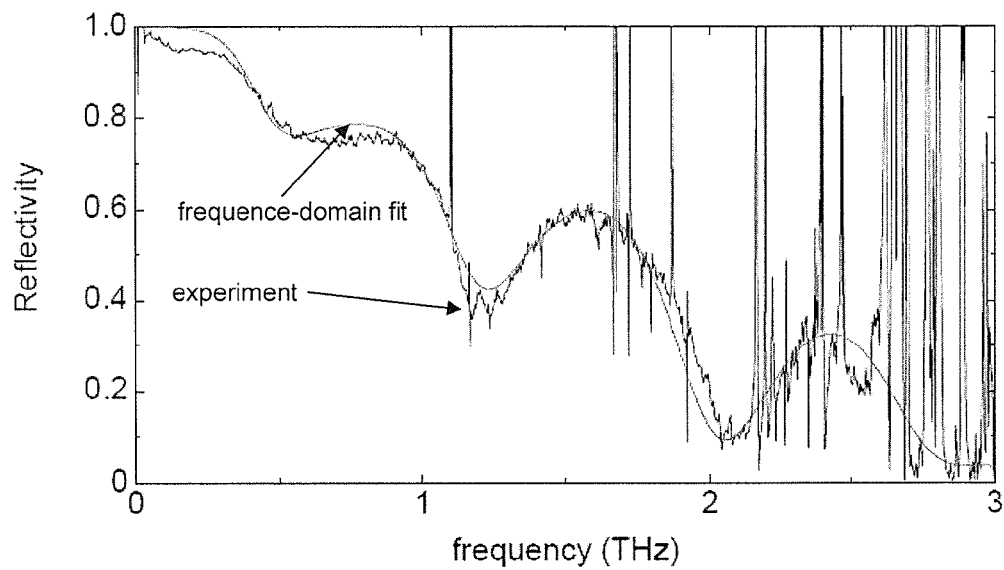
FIG. 6 is a diagram representing a response signal analogous to that of FIG. 5 but in frequency domain.

FIG. 6 shows the experimentally obtained reflectivity in the frequency domain (curve: experiment), i.e. the frequency-dependent response signal divided by the frequency-dependent reference signal. These latter two quantities are obtained for the same experimental conditions as in FIG. 5, in other words, they are the Fourier transforms of the respective curves shown in FIG. 5.

In FIGS. 5 and 6, the internal reflections inside the multilayer film (cf. FIG. 3) show up as oscillations in the frequency domain: Namely, the multiple reflections as shown in FIG. 3 give rise to characteristic periodicities in the response signal which resemble a beating pattern. These periodicities, in turn, give a straightforward handle inferring the layered structure of the coated body responsible for these multiple reflections by the method illustrated in FIG. 4. The periodicities in this embodiment, caused by interferences, are one example of a waveform that allows obtaining accurate and quickly converging results. In other embodiments, other waveforms may emerge that lack or visibly seem to lack such periodicities but that also allow inferring the layered structure.

Thus, the characteristic pattern of the response signal shown in FIGS. 5 and 6 (curve: experiment) contains information about the details of each layer, albeit in a highly convoluted form, from which prior art methods have been unable to extract this information. In particular, the prior art methods of peak subtraction and/or deconvolution of this complicated echo pulse train do not lead to a reliable thickness estimation of the individual layers, nor to the total stack thickness. In FIG. 5, for example, no clearly recognizable internal reflections are visible in the time-domain data. This would makes it difficult or even impossible for the prior art methods to determine individual peaks, and therefore to extract meaningful data.

The method of the invention, in contrast, is capable of extracting the relevant information from the THz response signal. Here, an embodiment of the method has been applied by simultaneously fitting the data in the time- and frequency-domain to a physical model by the steps described above with reference to FIG. 4. The resulting predicted response is shown as a best-fit curve (curve: time-domain fit) in time domain in FIG. 5 and in frequency domain (curve: frequence-domain fit) in FIG. 6. As can be seen from FIGS. 5 and 6, the fit describes the data to a very high accuracy, i.e. the best-fit (curve: time-domain fit respectively frequency-domain fit) approximates the experimental curve very well. The almost vertical spikes in the frequency spectrum of FIG. 6 are caused by a slight difference in air humidity between sample and reference, giving rise to spikes at the position of the absorptions lines of water. Overall, the good agreement of experimental data and model prediction is an indication of the quality and accuracy of the method.

From the best-fit parameters of the predicted waveform, the coating parameters 91 such as thickness d of each layer are obtained to high accuracy by the method described above (see e.g. description of FIG. 4).

The coating parameters (thicknesses) obtained from the fit by the method described above (see FIG. 4) include the following: 42.5 µm (thickness of clear coat), 22.3 µm (thickness of base coat), 31.9 µm (thickness of primer), with a total thickness of 96.7 µm.

Magnetic and mechanical conventional measurements indicate the total thickness of the coating to be 97±5 µm and 98±1 µm, respectively. Unfortunately, the individual layer thicknesses cannot be compared since the conventional measurements are unable to provide the thicknesses of individual layers. Nevertheless, the total thickness is in good agreement, which proves the consistency of the method according to the invention with the conventional approaches, within the limitations of these conventional approaches.

Figure 7:
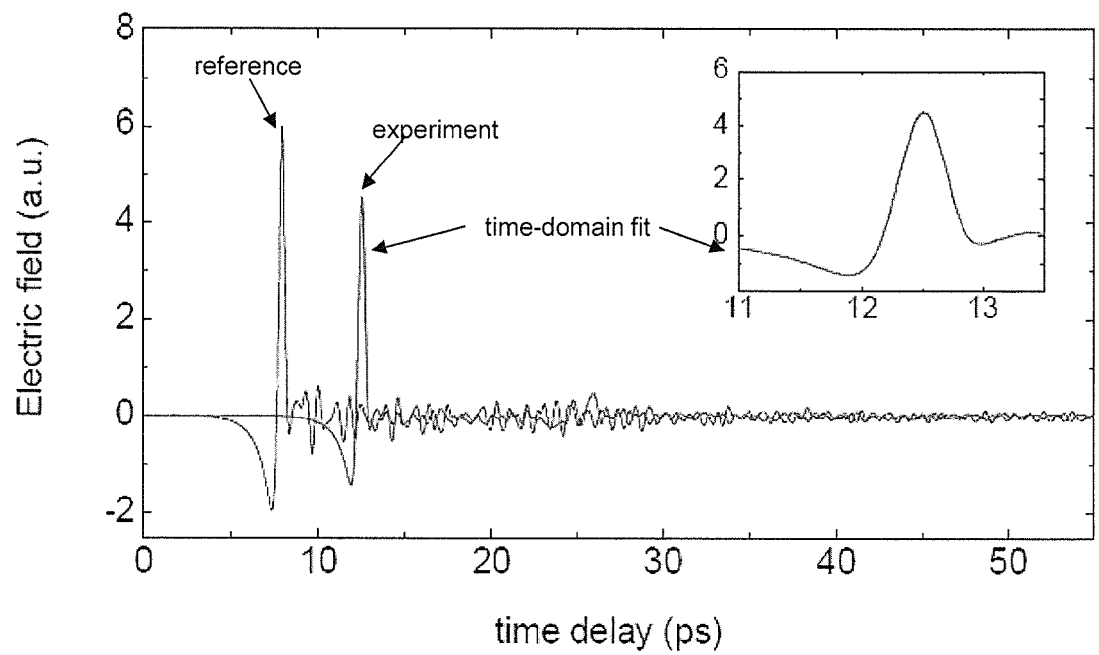
FIG. 7 is a diagram representing the response signal and related quantities measured by a system as shown in FIG. 1 in time domain.
Figure 8:
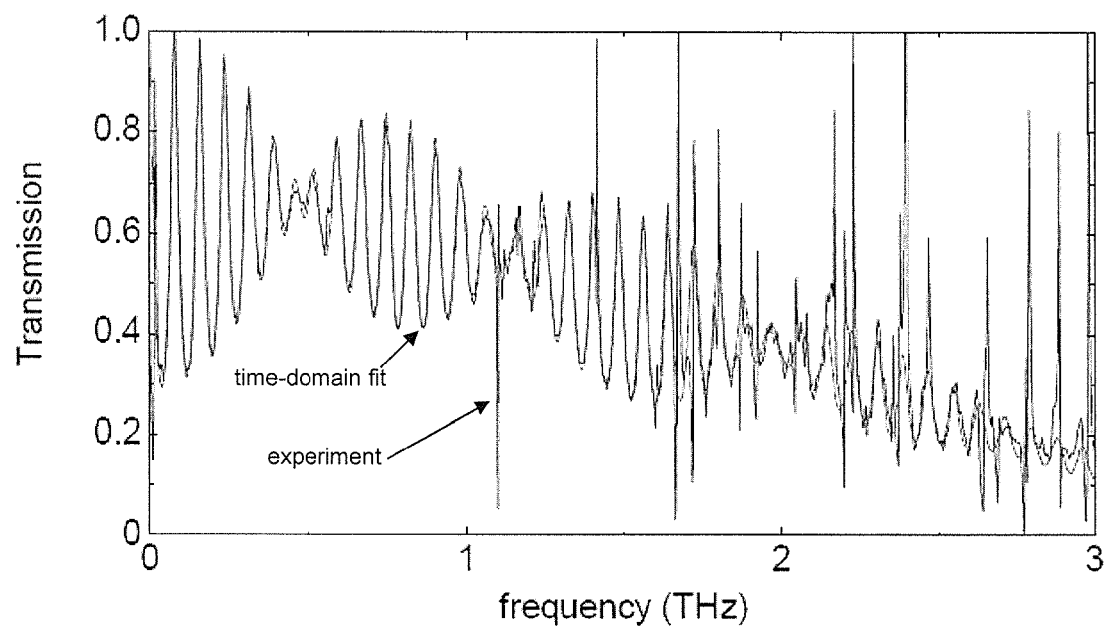
FIG. 8 is a diagram representing a response signal analogous to that of FIG. 7 but in frequency domain.

FIGS. 7 and 8 show a measurement similar to that in FIGS. 5 and 6, respectively, with the following differences: In FIGS. 7 and 8, a transparent substrate (crystalline silicon substrate) is used instead of the steel substrate of FIGS. 5 and 6. Also, a transmission measurement with a setup as shown in FIG. 2b is used. The expression in Eq. (2) has been adapted accordingly to account for the setup of FIG. 2b. Otherwise, the description of FIGS. 5 and 6 applies here as well.

The thicknesses that result from the analysis of the data of FIGS. 7 and 8 as described above are as follows: 45.7 µm (thickness of clear coat), 17.0 µm (thickness of base coat), 38.3 µm (thickness of primer), with a total thickness of 101.0 µm. Magnetic and mechanical conventional measurements indicate the total thickness to be 100±3 and 101±3 µm, respectively.

Figure 9A:
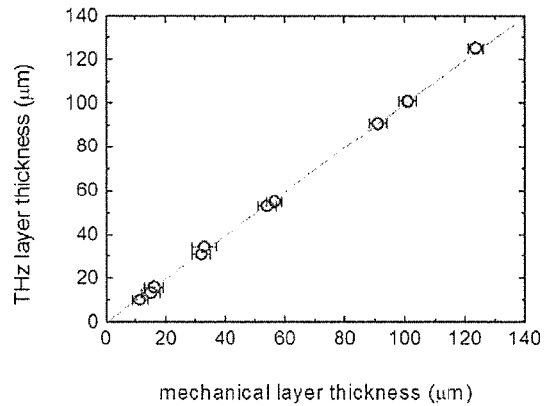
FIGS. 9a and 9b are diagrams in which thicknesses obtained by the method according to the present invention are compared with the respective thicknesses obtained by other methods are compared.
Figure 9B:
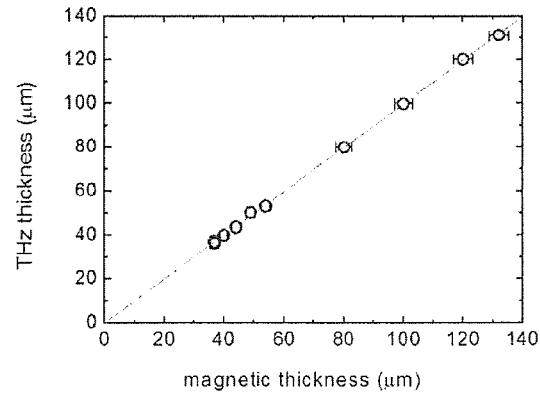

The method described herein has been applied in an analogous manner to further paint films, having coatings consisting of single, double and triple layers on a substrate. The thickness values obtained are compared to values obtained by conventional techniques and are shown in FIGS. 9a and 9b. In these Figures, the total thickness of the entire coating determined using THz technology (vertical axis) is compared to reference measurements using a conventional mechanical and magnetic technique on the same multilayers (horizontal axis of FIGS. 9a and 9b, respectively). The line is put as an indication of perfect matching, i.e. identity of both approaches.

In FIG. 9a, the substrate is silicon, and a measurement analogous to that of FIGS. 7 and 8 was carried out. In FIG. 9b, the substrate is steel, and a measurement analogous to that of FIGS. 5 and 6 was carried out. In both FIGS. 9a and 9b, the close correspondence between the values determined using the method described herein and the other approaches indicates the accuracy of the method described herein. The thinnest single layers on which the method has been applied were 37 μm on steel and 9.5 μm on silicon. As can be seen from FIGS. 9a and 9b, in all cases the method described herein gives precise results with accuracies better than 1 μm.

In the following, with reference to FIG. 10, further details regarding the determining of the type of paint of one or more individual layers is described as a further coating parameter(s). For this method, a reference dataset of relevant paints is stored in the system memory of the control unit. The reference set includes, for each of the paints, one or more optical properties such as a value or a range for a model parameter or coating parameter or a quantity derivable therefrom.

The one or more optical properties of each individual paint layer are determined during the fitting procedure and are subsequently compared to the reference dataset. The paint type is then determined as the entry from the reference dataset that is most consistent with the determined optical properties, e.g. has the least deviation from the determined optical properties or defines a range covering them.

Figure 10:
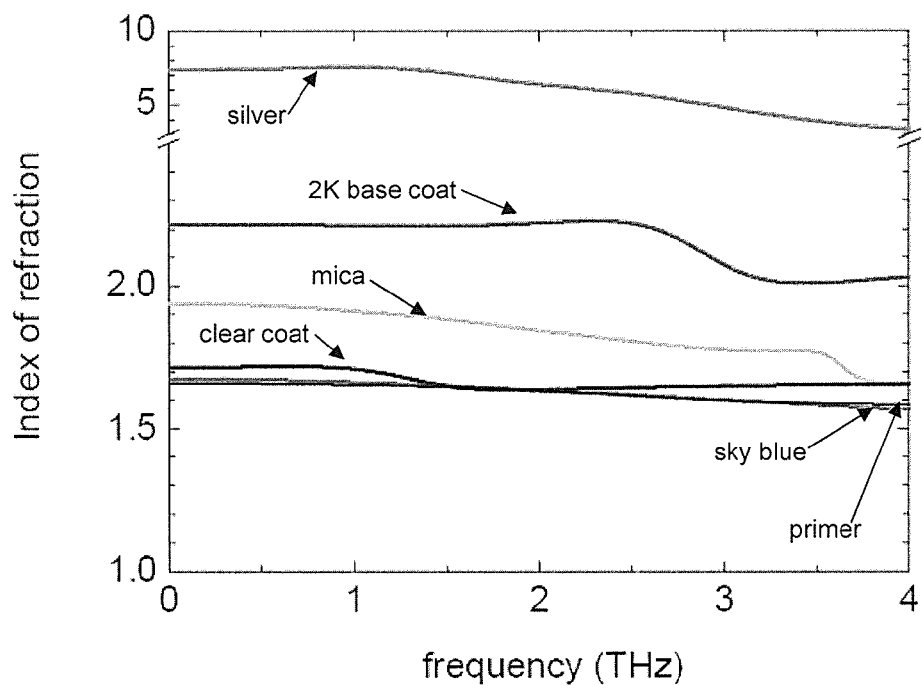
FIG. 10 is a diagram representing the frequency-dependent index of refraction of various types of layers which can be present in the polymeric coating.

To illustrate this aspect, FIG. 10 shows the optical properties, represented by the real part of the index of refraction, of six very common kinds of paint in the field of automotive paint. The kinds (types) of paint are: three waterborne basecoats (silver, mica, sky blue), and the three solvent borne paints (white primer, 2K blue base coat, clear coat). Here, the optical properties are given by the frequency-dependent index of refraction at THz frequencies, determined at room temperature.

One can see that the spectral dependence of each kind of paint is very different: silver paint contains aluminum particles which is reflected by a very large index of refraction as compared to clear coat and primer for instance. Due to the large spectral differences between the paints, spectra are quasiunique and the comparison of the optical properties with the ones of the reference dataset is well suited for determining the kind of paint.

Figure 11:
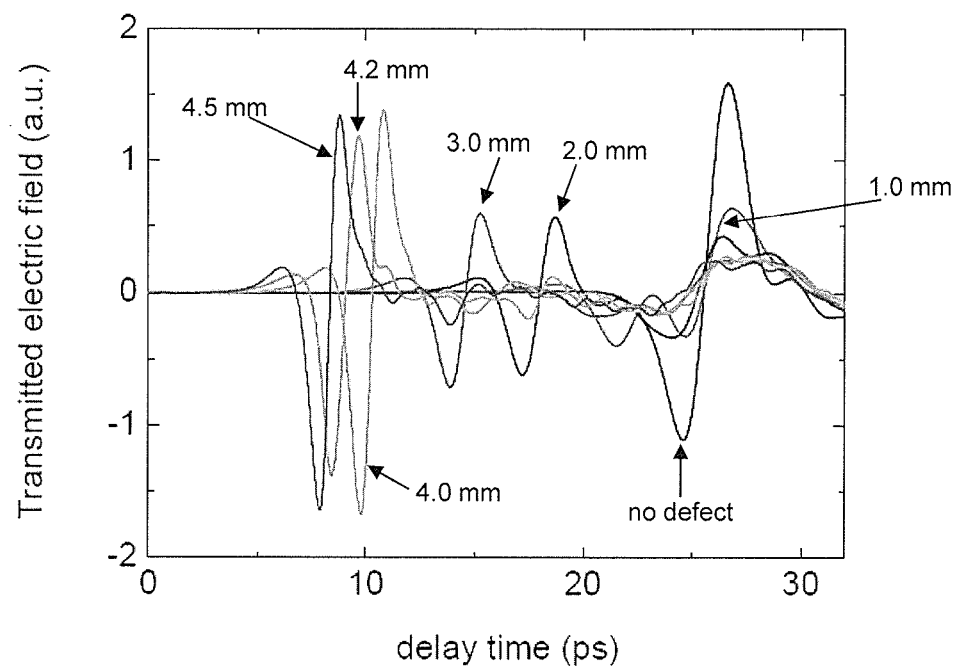
FIG. 11 is a diagram representing a response signal analogous to that of FIG. 7 for different sizes (thickness) of mechanical defects.
Figure 12:
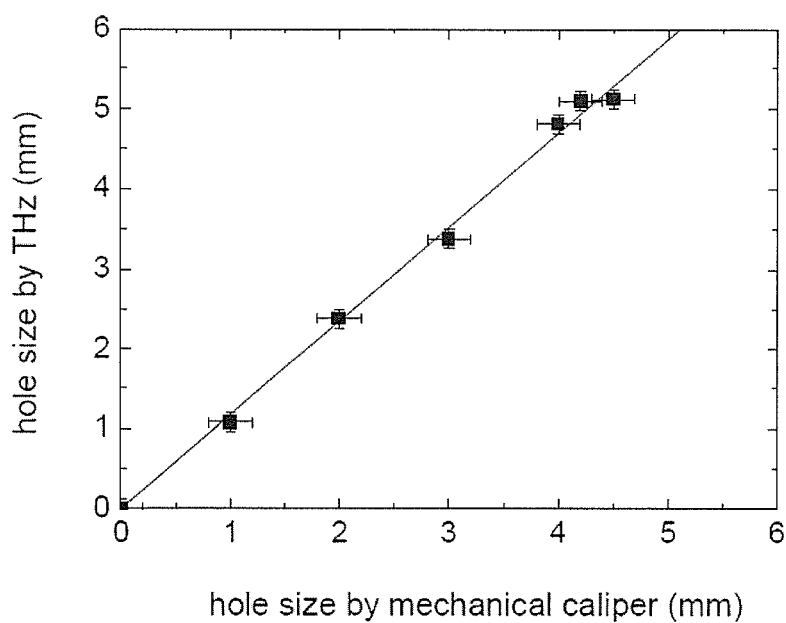
FIG. 12 is a diagram in which the sizes of mechanical defects obtained by the method according to the present invention are compared with the respective sizes obtained by other methods are compared.

With reference to FIGS. 11 and 12, a further aspect of a possible method according to the invention is now described. Namely, according to this aspect the number of layers of an unknown paint multilayer is determined as a further coating parameter. By the same method, it is optionally possible to identify possible defects below the paint, such as gas bubbles, instead of or in addition to the number of layers.

FIG. 11 shows the transmitted time-domain waveform for a coated body whose coating has one layer of white paint (~500 μm thickness) being applied on a glass fibre reinforced plastic substrate. The transmitted time-domain waveform is the transmitted electric field in time-domain at THz frequencies, i.e. data analogous to that of FIG. 7 and obtained in the same manner.

In the coated body, a gas bubble is present between the paint layer and the substrate. The gas bubble has been introduced intentionally as an indentation into the substrate, and represents a typical defect. In FIG. 11, the waveform is depicted for the case without gas bubble (curve: no defect) and for various gas bubbles of varying depth (between 0 and 4.5 mm, curves as indicated). Without gas bubble, the substrate thickness at the position of the defect is 5 mm. With gas bubble, the substrate thickness is reduced such that the thickness of the substrate plus gas bubble is constant at 5 mm. Hence, for example, the substrate thickness is reduced to 0.5 mm in the case of a 4.5 mm thick defect.

From the waveforms in FIG. 11 it, is already visually clear that a medium with a much lower index of refraction is present below the paint since the pulse train is shifted to shorter time delays. This immediately shows the suitability of the method for defect detection: The defect is detected as a further "layer" of low index of refraction relative to the paint. Due to the high difference in index of refraction with the surrounding paint layers, the optical contrast is high, and reliable detection of the defect is possible.

Hence, according to an aspect of the invention, a defect is detected by determining the number of layers as a function of location, and by registering a local variation in the number of layers. The defect area may then be determined as an area having an increased number of layers relative to its surrounding. Thereby, the size of the defect may be determined as the size of this area. Within this area, also the index of refraction of the defect may be determined, and therefrom optionally a type of defect may be determined.

The result of applying the method of detecting a defect is shown in FIG. 12. Herein, the defect size as determined by the method described herein (vertical axis) is compared to the size determined from mechanical measurements (horizontal axis). The resulting data points of FIG. 12 lie close to a straight line which is a linear fit through the result. This illustrates the consistency and reproducibility of this method.

The methods according to the invention are especially applicable in the case that the polymeric coating is a paint film having one or more layers of paint. One use of the method and system is for the analysis of a painted automobile body or a painted automobile component. Another use is for the analysis of a train body/component, an aircraft body/component such as an aircraft fuselage, aircraft wing, or the like. Another use is for the analysis of a wind turbine component, in particular of a painted blade of a wind turbine. The substrate body may comprise at least one of a ferrous metal, a nonferrous metal, and a fiber composite material. For example, an application of the present aspect of the invention is defect detection in blades of wind turbines e.g. for off-shore purposes. Here, the coated body is a wind turbine blade containing a defect below the paint.

While the foregoing is directed to embodiments, other and further embodiments may be devised without departing from the basic scope determined by the claims.

What is claimed is:

1. A method of characterizing a coated body by at least one coating parameter based on fitting to a physical model, wherein the coated body comprises a substrate coated by a polymeric coating, the polymeric coating having at least one layer, and wherein the method being carried out by a sensor system in a non-contact manner, the sensor system comprising an emitter system for emitting THz radiation, a detector system for detecting THz radiation, and a processing unit operationally coupled to the emitter system and the detector system, the method comprising:

emitting, by the emitter system, a THz radiation signal towards the coated body such that the THz radiation interacts with the polymeric coating;

detecting, by the detector system, a response signal being the detected THz radiation signal having interacted with the polymeric coating;

determining model parameters of the physical model by optimizing the model parameters such that a predicted response signal of the physical model is fitted to the detected response signal, the model parameters being indicative of optical properties of the polymeric coating describing the interaction of the THz radiation signal with the polymeric coating, the determined model parameters including a parameterization of the index of refraction of the at least one layer;

determining, from the determined model parameters, the at least one coating parameter, wherein the at least one coating parameter includes a thickness of the polymeric coating.

2. The method according to claim 1, wherein the polymeric coating is a multi-layered coating having at least a first layer and a second layer, and wherein the at least one coating parameter is a plurality of coating parameters including a thickness of the first layer and of the second layer.

3. The method according to claim 1, wherein the coating is a paint film, and comprises at least one of the following layers:
(a) an e-coat layer
(b) a primer layer
(c) a base coat layer
(d) a clear coat layer.

4. The method according to claim 1, wherein the coated body is one of an automobile component, a train component, an aircraft component, and a wind turbine component.

5. The method according to claim 1, wherein the substrate body comprises at least one of a ferrous metal, a non-ferrous metal, and a fiber composite material.

6. The method according to claim 1, wherein the predicted response signal of the physical model is fitted to the detected response signal by an iterative procedure comprising the steps:
(a) calculating a simulated response signal based on the physical model using an initial guess for the model parameters;
(b) calculating an error function expressing a deviation between the predicted response signal and the detected response signal;
(c) iterating steps (a) and (b), whereby the model parameters are varied until the error function satisfies a best-fit criterion,
(d) obtaining the fitted parameters as the final parameters satisfying the best-fit criterion in step (c), and calculating at least one of the one or more coating parameters from the fitted parameters.

7. The method according to claim 6, wherein the error function has a frequency dependent sensitivity.

8. The method according to claim 6, wherein step (a) includes calculating a simulated response signal both in time domain and in frequency domain; step (b) includes calculating the error function as a function of a time-domain error function component and a frequency-domain error function component.

9. The method according to claim 1, wherein the at least one coating parameter is a plurality of coating parameters further including at least one of the following:
(a) a paint type identifier characterizing a type of paint contained in at least one layer of the coating, the paint type identifier characterizing the type of paint according to at least one of the following characteristics: water-borne or solvent-borne paint; a characteristic of the absorption spectrum; a type of pigment, a type of additive, and a type of solvent;
(b) a specific weight of at least one layer of the coating, wherein the weight of the layer is optionally obtained from at least one of the index of refraction and the paint type identifier of the layer;
(c) a defect parameter indicating a defect in at least one layer of the coating;
(d) a total number of layers of the coating.

10. The method according to claim 1, wherein all of the one or more coating parameters are determined from a single response signal.

11. The method according to claim 1, wherein the emitter system and the detector system are arranged on the same side of the coated body for carrying out a reflection measurement.

12. The method according to claim 1, further comprising inputting a reference signal sequence in the physical model, wherein the reference signal sequence describes the emitted THz radiation signal not having interacted with the coated body.

13. The method according to claim 1, wherein the determined model parameters include a parameterization of the index of refraction of the first layer such that the index of refraction has a dependence on frequency, wherein the index of refraction preferably includes a frequency-dependent contribution describing a resonance, and wherein the frequency-dependent contribution is particularly preferably expressable as $$\omega_p^2/(\omega_0^2-\omega^2-i\gamma\omega),$$

wherein $\omega$ is the frequency, $\omega_0$ is a peak frequency, $\omega_p$ is a plasma frequency, $\gamma$ is a damping coefficient, and i is the imaginary unit.

14. The method according to claim 1, further comprising emitting, by the emitter system, a THz radiation signal towards a coated body such that the THz radiation interacts with the polymeric coating, wherein the coated body comprises a substrate coated by a paint film.

15. A sensor system for characterizing a coated body, the sensor system comprising:
an emitter system for emitting THz radiation towards the coated body;
a detector system for detecting THz radiation coming from the coated body;
a positioning system for positioning the emitter system and the detector system relative to the painted body; and
a processing unit operationally coupled to the emitter system and the detector system, wherein
the sensor system is configured for performing a method of characterizing a coated body by at least one coating parameter based on fitting to a physical model, wherein
the coated body comprises a substrate coated by a polymeric coating, the polymeric coating having at least one layer,
the method comprising:
emitting, by the emitter system, a THz radiation signal towards the coated body such that the THz radiation interacts with the polymeric coating;
detecting, by the detector system, a response signal being the detected THz radiation signal having interacted with the polymeric coating;
determining model parameters of the physical model by optimizing the model parameters such that a predicted response signal of the physical model is fitted to the detected response signal, the model parameters being indicative of optical properties of the polymeric coating describing the interaction of the THz radiation signal with the polymeric coating, the determined model parameters including a parameterization of the index of refraction of the at least one layer;

determining, from the determined model parameters, the at least one coating parameter, wherein the at least one coating parameter includes a thickness of the polymeric coating.

16. The system according to claim 15, wherein the polymeric coating is a paint film.

17. A method of characterizing a coated body by at least one coating parameter based on fitting to a physical model, wherein the coated body comprises a substrate coated by a polymeric coating, the polymeric coating having at least one layer, wherein the method being carried out by a sensor system in a non-contact manner, the sensor system comprising an emitter system for emitting THz radiation, a detector system for detecting THz radiation, and a processing unit operationally coupled to the emitter system and the detector system, and wherein the emitter system and the detector system are arranged on the same side of the coated body for carrying out a reflection measurement;

the method comprising:

emitting, by the emitter system, a THz radiation signal towards the coated body such that the THz radiation interacts with the polymeric coating;

detecting, by the detector system, a response signal being the detected THz radiation signal having interacted with the polymeric coating;

determining model parameters of the physical model by optimizing the model parameters such that a predicted response signal of the physical model is fitted to the detected response signal, the model parameters being indicative of optical properties of the polymeric coating describing the interaction of the THz radiation signal with the polymeric coating, the determined model parameters including a parameterization of the index of refraction of the at least one layer;

determining, from the determined model parameters, the at least one coating parameter, wherein the at least one coating parameter includes a thickness of the polymeric coating;

detecting a plurality of response signals by the detector system at at two different positions of the detector system relative to at least one of the emitter system and the surface of the coated body, at least one of the positions being away from a direct optical path defined by the emitter system and the surface of the coated body; and determining a surface roughness of the surface of the coated body based on the plurality of detected response signals.

\* \* \* \* \*